United States Patent [19]

Romanelli et al.

[11] Patent Number: 4,755,168
[45] Date of Patent: Jul. 5, 1988

[54] MEDICAL DRAINAGE PUMP WITH IRRIGATION

[76] Inventors: Pat Romanelli, 224 Brook St.; Robert Romanelli, 242 Brook St., both of Harrington Park, N.J. 07640

[21] Appl. No.: 6,771

[22] Filed: Jan. 27, 1987

[51] Int. Cl.$^4$ ............................................... A61M 1/03
[52] U.S. Cl. ......................................... 604/34; 604/31; 128/DIG. 12; 417/476
[58] Field of Search ........................... 604/31, 118–120, 604/151–153, 30, 34–35; 128/DIG. 12, DIG. 13; 417/474, 475, 476, 477

[56] References Cited

U.S. PATENT DOCUMENTS 3,932,065 1/1976 Ginsberg et al. ................. 604/34 X
4,385,630 5/1983 Gilcher et al. ................... 604/35 X
4,496,342 1/1985 Banho ............................... 604/31 X
4,626,239 12/1986 Ardizzone ........................... 604/31
4,650,457 3/1987 Morioha et al. ....................... 604/4

*Primary Examiner*—Edward M. Coven
*Attorney, Agent, or Firm*—Thomas R. Morrison

[57] ABSTRACT

A medical drainage and irrigation system employs a reversible peristaltic pump to perform both drainage and irrigation. A motor control system independently controls the duty cycle and flow rate during drainage and irrigation using an electronic control to transfer the pumping direction between drainage and irrigation. A loop comprising a flow control valve assembly and external tubes connected thereto may be removed as an assembly for cleaning or discard.

4 Claims, 3 Drawing Sheets

MEDICAL DRAINAGE PUMP WITH IRRIGATION

BACKGROUND OF THE INVENTION

The present invention relates to medical drainage pumps and, more particularly, to medical drainage pumps having means for controlled drainage of body fluids under suction and also having means for periodically infusing an irrigating fluid for clearing blood, mucous, or other material from the system. In addition, the medical drainage pumps are useful for controlled infusion of medication into the system.

Medical drainage pumps are conventionally used during surgery or medical treatment to drain body fluids from body cavities. One such medical drainage pump is disclosed in my prior U.S. Pat. No. 3,429,313, in which a double-action vacuum/pressure pump produces both a vacuum for drainage and an air pressure for controlling irrigation using an intermediate fixed-volume irrigation cylinder. Transfer between drainage and irrigation is controlled by a plurality of cams on a rotating wheel. The cams contact a lever, thereby operating a spool valve for cutting off drainage and directing air pressure to the irrigation cylinder. The irrigation cylinder then executes a single cycle for infusing a predetermined quantity of irrigation fluid into the body cavity.

The control system in the above patent requires numerous mechanical components thereby adding to the cost. The cam-type control lacks flexible control of drainage and irrigation.

OBJECTS AND SUMMARY OF THE INVENTION

Accordingly, it is an object of the invention to provide a medical drainage pump with an irrigation capability which overcomes the drawbacks of the prior art.

It is a further object of the invention to provide a medical drainage pump with irrigation in which switching between drainage and irrigation functions is simplified.

It is a still further object of the invention to provide a medical drainage and irrigation pump having a flexible control system enabling independent control of drainage and irrigation cycles and speeds.

It is a further object of the invention to provide apparatus for the automatic introduction into the body cavity of medication such as, for example, antibiotics, anti inflammatory drugs, fibrinolydic drugs or ice water to control internal bleeding.

Briefly stated, the invention provides a medical drainage and irrigation system employing a reversible peristaltic pump to perform both drainage and irrigation. A motor control system independently controls the duty cycle and flow rate during drainage and irrigation using an electronic control to transfer the pumping direction between drainage and irrigation. A loop comprising a flow control valve assembly and external tubes connected thereto may be removed as an assembly for cleaning or discard.

According to an embodiment of the invention, there is provided a medical drainage and irrigation system comprising: a peristaltic pump, a variable-speed and reversible-direction motor driving the peristaltic pump, a flow control valve assembly at a first end of the peristaltic pump, a patient tube at a second end of the peristaltic pump, the flow control valve including means for permitting irrigation fluid to flow from an irrigating fluid reservoir therethrough into the peristaltic pump when the motor drives the peristaltic pump in a first direction and for permitting body fluid to flow from the peristaltic pump to flow therethrough toward a drainage receptacle when the motor drives the peristaltic pump in the reverse direction, the flow control assembly including means for preventing the irrigation fluid from flowing therethrough toward the irrigating fluid reservoir, and means for controlling the speeds and direction of the motor, whereby, a duty ratio and pumping rate of the peristaltic pump is controlled.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
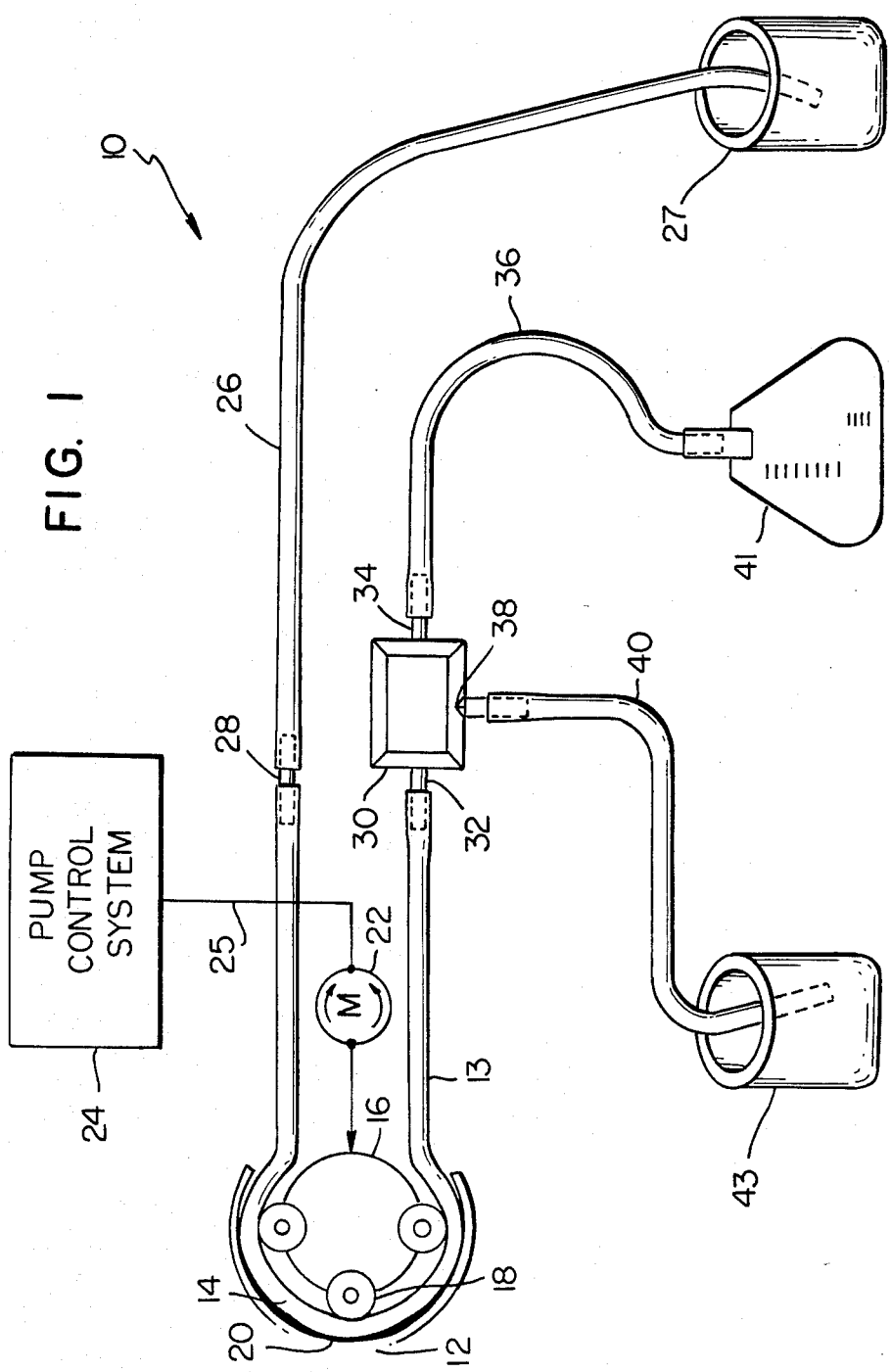
FIG. 1 is a simplified schematic diagram of a drainage and irrigation system according to an embodiment of the invention.

Referring now to FIG. 1, there is shown, generally at 10, a medical drainage and irrigation system according to an embodiment of the invention. A roller-type peristaltic pump 12 includes a flexible tube 13 of a resilient plastic material. Part of flexible tube 13 is formed into a loop 14. A generally circular plate 16 includes a plurality of rollers spaced at a common radius about its circumference. A part-circular backup wall 20 surrounds a portion of loop 14. A pump control system 24 produces control signals for application on a control line 25 to reversible motor 22. Responsive to its control signals reversible motor 22 rotates plate 16 in a selected direction, and at a selected speed.

As plate 16 rotates, rollers 18 squeeze loop 14 against part-circular backup wall 20 thus urging fluid flow in loop 14 in the direction of rotation of plate 16.

A patient tube 26 is attached at one end to flexible tube 13 using, for example, a coupling 28. The other end of patient tube 26 may be connected to a conventional catheter (not shown) or other device for entry into an organ 27 of the patient needing drainage and irrigation. Reference is made to my above-referenced U.S. Patent, the disclosure of which is herein incorporated by reference, for conventional patient interface techniques. Since the referenced patent contains a full disclosure of patient interface techniques, further discussion thereof in the present disclosure would be redundant and is therefore omitted.

Figure 2:
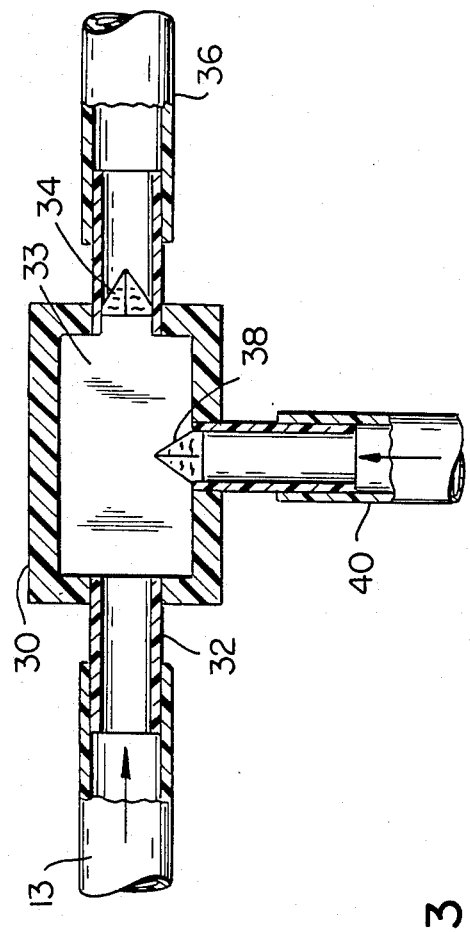
FIG. 2 is a detailed view of a check valve assembly of FIG. 1.

Referring now also to FIG. 2, a check valve assembly 30 includes a coupling 32 connected to a second end of flexible tube 13. A flow chamber 33 in check valve assembly 30 interconnects coupling 32 with a drainage check valve 34 and an irrigation check valve 38. Drainage fluid check valve 34 is connected to a drainage fluid line 36 which is conventionally vented to drainage fluid reservoir 41 such as, for example, a bottle or bag. Irrigation fluid check valve 38 is connected through an irrigation fluid line 40 to an irrigating fluid reservoir 43 such as, for example, a bottle or bag.

Any suitable type of one-way valves may be used in check valve assembly including, for example, the duckbill type shown. Other suitable types of check valves may be substituted without departing from the spirit and scope of the invention.

When plate 16 is rotated in a counter-clockwise direction, roller-type peristaltic pump 12 tends to apply suction to patient tube 26 and thereby drain fluids from organ 27. A resulting positive pressure created in flow chamber 33 closes irrigation fluid check valve 38 and permits drainage fluid to pass through drainage fluid check valve 34 and drainage fluid line 36 to drainage fluid reservoir 41. When plate 16 is rotated in the clockwise direction, a resulting negative pressure in flow chamber 33 applies suction to drainage fluid check valve 34 thus drawing irrigation fluid through irrigation check valve 38, which then passes through roller-type peristaltic pump 12 and patient tube 26 to organ 27. Thus, the direction of rotation of the reversible motor 22 driving plate 16 directly controls the function, drainage or irrigation, being performed. In addition, the rotational speed of plate 16 controls the fluid flow rate in each function.

Figure 3:
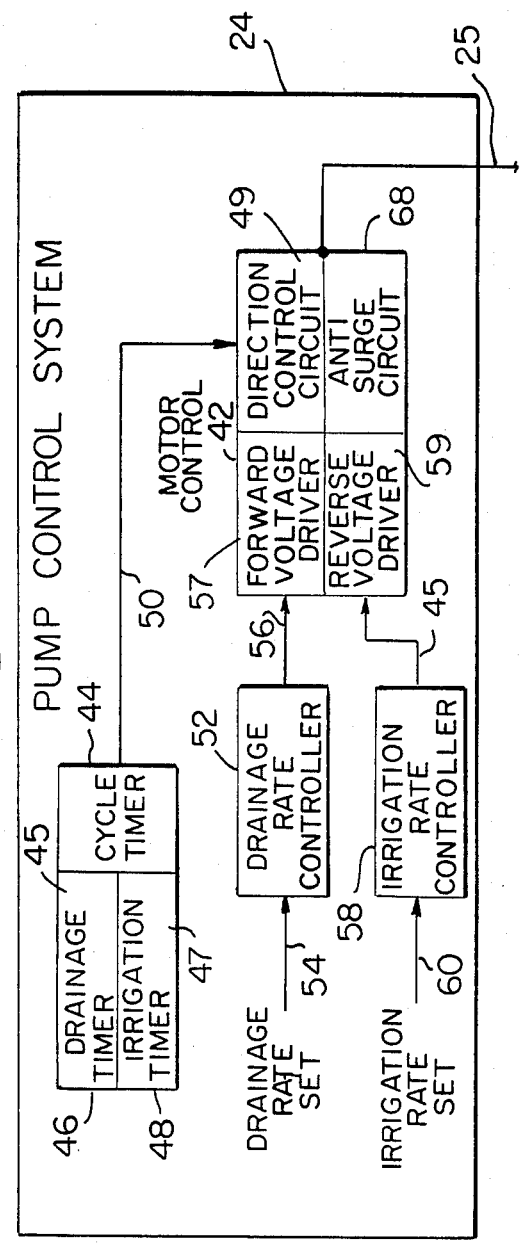
FIG. 3 is a schematic diagram of a pump control system of FIG. 1.

Referring now to FIG. 3, pump control system 24 includes a motor control 42 for applying appropriate voltage to reversible motor 22. The direction of rotation, and the resulting periods of drainage and irrigation cycles, is controlled by a cycle timer 44. Cycle timer 44 includes a drainage timer 45 receiving a signal on a line 46 representing the fraction of total time for the drainage function and an irrigation timer 47 receiving a signal on a line 48 representing the fraction of total time for the irrigation function. The resulting timer output signals are applied on a line 50 to a direction control circuit 49 in motor control 42.

The rotational speed of reversible motor 22 during drainage, and the resultant drainage fluid flow rate during drainage, is controlled by a drainage rate controller 52 to apply a drainage rate signal on a line 56 to motor control 42. Similarly, the rotational speed of reversible motor 22 during irrigation, and the resultant irrigation fluid flow rate is controlled by an irrigation rate control 42. Drainage rate controller 52 receives a control voltage on a line 54 generated by conventional means such as, for example, a variable resistor (not shown). In response to its input, drainage rate controller applies a related voltage on a line 56 to a forward voltage driver 57 in motor control 42. Any convenient conventional apparatus may be employed in drainage rate controller 52 such as, for example, an operational amplifier with suitable input and feedback impedances (not shown). Irrigation rate controller 58, which may contain the same apparatus as drainage rate controller 52, receives an irrigation rate signal generated, for example, by a variable resistor (not shown), on a line 60. A corresponding irrigation signal is applied on a line 45 to a reverse voltage driver 59 in motor control 42.

Although any suitable apparatus may be employed in motor control 42, in one embodiment of the invention, forward voltage driver 57 and reverse voltage driver 59 are relay contacts and directional control circuit 49 is a bi-directional relay coil controlling the relay contacts. In the absence of a control signal on line 50, all relay contacts are open. When drainage timer 45 applies a drainage command on line 50, the relay coil in directional control circuit is energized in a direction effective to connect relay contacts in forward voltage driver 57 to communicate the signal on line 56 to reversible motor 22. Reversible motor 22 then rotates in the direction effective for producing drainage and at a speed determined by the signal on line 56. Similarly, when irrigation timer 47 applies an irrigation command on line 50, the relay coil in directional control circuit is energized in a direction effective to connect relay contacts in reverse voltage driver 57 to communicate the signal on line 45 to reversible motor 22. Reversible motor 22 then rotates in the direction effective for producing irrigation and at a speed determined by the signal on line 45.

From the foregoing, it will be recognized that the fraction of total time during which irrigation and drainage are performed are established independently of each other with the constraint that the sum of the duty ratios of the two functions cannot exceed one. Furthermore, a speed of directional motor 22 during irrigation is controlled independently of the speed during drainage, as may be required for certain treatments.

An anti-surge circuit 68 limits the acceleration and deceleration rate of reversible motor 22. In an analog embodiment of the invention anti-surge circuit 68 preferably contains an integration circuit having a capacitance to limit the rate at which its output may increase or decrease regardless of the rate at which its input increases or decreases. This avoids, for example, a sharp increase (surge) in acceleration of reversible motor 22 when an energizing signal is applied or changed rapidly.

In this manner, drainage and irrigation may be performed in any sequence, at any combination of rates, and at any desired duty ratio under control of cycle timer 44. That is, drainage may be performed, for example, 25 percent of the time, with reversible motor 22 energized for drainage during five of every twenty minutes, and irrigation may be performed for a few seconds between, for example, every second drainage cycle. The flow rates during the drainage and irrigation cycles are independently controllable. The apparatus may be inactive during the remainder of the time.

It would be clear to one skilled in the art that a programmed series of drainage and irrigation cycles could be controlled in which the duty ratios of drainage and irrigation may change with time, or in response to measured inputs (not shown) for a particular treatment.

The illustrated and described apparatus may be realized using any convenient type of hardware. For example, the electronic elements of motor control system 24 may be discrete electronic components and control circuit maybe a conventional electromechanical device such as a relay. Flexibility of the apparatus may be enhanced, however, by employing an analog or digital computer to control at least the functions of cycle timer 44.

In a preferred embodiment, a microprocessor controller performs substantially all of the functions of motor control system 24 with control signals on lines 46, 48, 54 and 60 being digital signals generated, for example, on a user keyboard or being entered from a storage medium such as, for example, magnetic tape or disk, or solid state random access memory (RAM). A digital embodiment of the invention may control the speed of reversible motor 22 in any convenient manner such as, for example, pulse-width modulation of a constant-amplitude source. Alternatively, reversible motor 22 may be a stepping motor, whose speed and direction are controlled by the rate and phase relationships of the signals applied thereto. The digital processor, in either case, generates the signal for controlling the speed of reversible motor 22. The function of anti-surge circuit 68 may be performed by programming the acceleration and deceleration within the digital processor with the output pulse-width modulated signals or stepping motor control signal being suitably programmed to effect the desired rates of acceleration and deceleration.

It will be evident to one skilled in the art that the disclosed invention provides a simple apparatus capable of performing the functions of prior art drainage and irrigation devices with substantially improved simplicity, controllability and programmability. In addition, the portions of medical drainage and irrigation systems in FIG. 1 consisting of flexible tube 13, patient tube 26, coupling 28, check valve assembly 30, drainage fluid line 36 and irrigation fluid line 40 may be sufficiently inexpensive to contemplate discarding these elements after use rather than investing the time and expense required for sterilization. Removal of these elements as an assembly requires only that loop 14 be withdrawn from roller-type peristaltic pump 12. Easy provision for such withdrawal may be made in any convenient manner.

Having described preferred embodiments of the invention with reference to the accompanying drawing, it is to be understood that the various changes and modifications may be effected therein by one skilled in the art without departing from the scope or spirit of the invention as defined in the appended claims.

What I claim is:

1. A medical drainage and irrigation system comprising:
   a peristaltic pump having a flexible tube passing therethrough;
   a variable-speed and reversible-direction motor driving said peristaltic pump;
   a check valve assembly on said flexible tube;
   a patient tube at an end of said flexible tube;
   said check valve assembly including means for permitting irrigating fluid to flow from an irrigation fluid reservoir through said peristaltic pump when said motor drives said peristaltic pump in a first direction and for permitting body fluid to flow from said peristaltic pump therethrough toward a drainage receptacle when said motor drives said peristaltic pump in a reverse direction;
   said check valve assembly including means for preventing said irrigation fluid from flowing therethrough toward said drainage fluid receptacle and for preventing said body fluids form flowing therethrough toward said irrigating fluid reservoir; and
   means for controlling a speed, a duration and direction of said motor whereby a duty ratio and a pumping rate of said peristaltic pump is controlled.

2. Apparatus according to claim 1 wherein said means for controlling includes:
   a cycle timer;
   said cycle timer including means for independently controlling a first duty cycle of said drainage and a second duty cycle of said irrigation;
   a drainage rate controller;
   said drainage rate controller including means for controlling a speed of said peristaltic pump during drainage, whereby a flow rate during drainage is controlled;
   an irrigation rate controller; and
   said irrigation rate controller including means for controlling a speed of said peristaltic pump during irrigation; and
   said drainage rate controller and said irrigation rate controller being independently controllable.

3. Apparatus according to claim 1 wherein said means for controlling a speed and direction includes means for controllably maintaining said peristaltic pump in a quiescent condition, whereby a total duty ratio of said drainage and said irrigation are controllable.

4. Apparatus according to claim 1 wherein said means for controlling a speed and direction includes a digital processor.

* * * * *